(12) United States Patent
Wu et al.

(10) Patent No.: US 10,337,987 B2
(45) Date of Patent: Jul. 2, 2019

(54) RADIAL-LINE SCANNING SPECTROMETER WITH TWO-DIMENSIONAL SENSOR

(71) Applicants: CANON USA INC., Melville, NY (US); THE GENERAL HOSPITAL CORPORATION, Boston, MA (US)

(72) Inventors: Tzu-Yu Wu, Malden, MA (US); Mitsuhiro Ikuta, Cambridge, MA (US); Dongkyun Kang, Tucson, AZ (US); Guillermo J. Tearney, Cambridge, MA (US)

(73) Assignees: Canon U.S.A., Inc., Melville, NY (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 15/625,899

(22) Filed: Jun. 16, 2017

(65) Prior Publication Data

US 2018/0364154 A1    Dec. 20, 2018

(51) Int. Cl.
*G01J 3/00*    (2006.01)
*G01N 21/31*    (2006.01)
(Continued)

(52) U.S. Cl.
CPC ............. *G01N 21/31* (2013.01); *A61B 1/00* (2013.01); *G02B 23/2469* (2013.01);
(Continued)

(58) Field of Classification Search
CPC ........ G01J 3/00; G01J 3/02; G01J 3/28; G01J 3/44; G01N 21/64; G01N 21/65
See application file for complete search history.

(56) References Cited

U.S. PATENT DOCUMENTS 6,377,349 B1 *  4/2002  Fercher ............. G01B 11/2441
                                                356/479
6,529,769 B2    3/2003  Zigler
(Continued)

FOREIGN PATENT DOCUMENTS

DE    102013005173 A1    10/2014
JP       2007087954 A     4/2007
(Continued)

OTHER PUBLICATIONS

Tearney, G., et al., "Spectrally encoded minature edoscopy", Optics Letters, Mar. 15, 2002, pp. 412-414, vol. 27, No. 6.
(Continued)

*Primary Examiner* — Abdullahi Nur
(74) *Attorney, Agent, or Firm* — Canon U.S.A., Inc., IP Division

(57) ABSTRACT

An apparatus for spectrally encoded endoscopy (SEE) comprising an illumination element, a detection light guiding element, a rotary element, and a two-dimensional sensor. The illumination element is configured to direct an illumination light beam towards a sample. The detection light guiding element is configured to collect a reflected light beam from the sample. At least one of the illumination element and the detection light guiding element is configured to spectrally dispersed the illumination light beam or the reflected light beam, respectively. The rotary element is configured to rotate or oscillate the reflected light beam. The reflected light beam is guided from the rotary element to the two-dimensional sensor.

28 Claims, 7 Drawing Sheets

(51) Int. Cl.
    *G02B 23/24*    (2006.01)
    *G02B 23/26*    (2006.01)
    *A61B 1/00*    (2006.01)

(52) U.S. Cl.
    CPC ..... *G02B 23/26* (2013.01); *G01N 2201/0633* (2013.01); *G01N 2201/08* (2013.01)

(56) References Cited

U.S. PATENT DOCUMENTS

| | | |
|---|---|---|
| 7,336,353 B2 | 2/2008 | Brady et al. |
| 7,705,992 B2 | 4/2010 | Hatori et al. |
| 7,898,656 B2 | 3/2011 | Yun et al. |
| 7,982,879 B2 * | 7/2011 | Desjardins ......... G01N 21/4795 356/477 |
| 8,045,177 B2 | 10/2011 | Tearney et al. |
| 8,818,149 B2 | 8/2014 | Shishkov et al. |
| 2007/0213618 A1 | 9/2007 | Li et al. |
| 2009/0309957 A1 | 12/2009 | Ge et al. |
| 2011/0275899 A1 | 11/2011 | Tearney et al. |
| 2012/0194661 A1 | 8/2012 | Lee et al. |
| 2014/0276032 A1 | 9/2014 | Majewski et al. |
| 2014/0285644 A1 | 9/2014 | Richardson et al. |

FOREIGN PATENT DOCUMENTS

| | | |
|---|---|---|
| WO | 2015/116939 A1 | 8/2015 |
| WO | 2015/116951 A1 | 8/2015 |
| WO | 2017/024234 A1 | 2/2017 |

OTHER PUBLICATIONS

Zeidan A., et al., "Miniature forward-viewing spectrally encoded endoscopic probe", Optics Letters, Aug. 15, 2014, pp. 4871-4874, vol. 39, No. 16.

Yelin, D. et al., "Volumetric sub-surface imaging using spectrally encoded endoscopy", Optics Express, Feb. 1, 2008, pp. 1748-1757, vol. 16, No. 3.

* cited by examiner

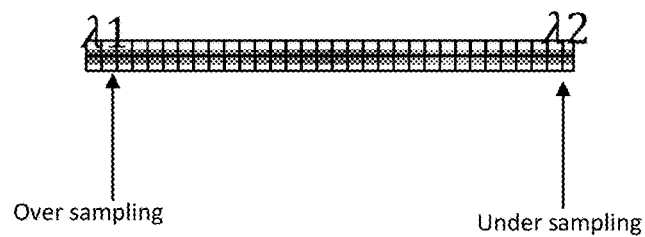
Fig. 1(c)
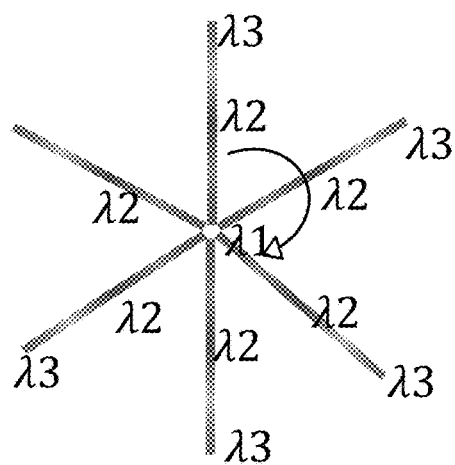 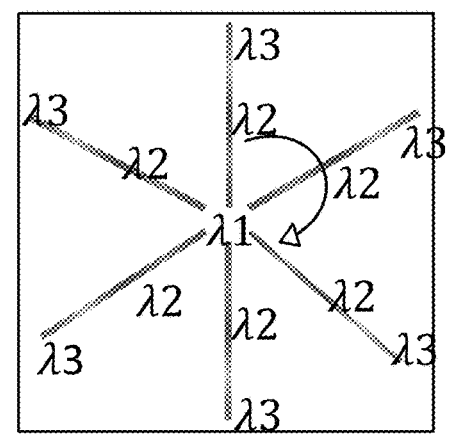
Fig. 2(a)          Fig. 2(b)

RADIAL-LINE SCANNING SPECTROMETER WITH TWO-DIMENSIONAL SENSOR

BACKGROUND

Field of the Disclosure

The present disclosure relates in general to a spectrally encoded endoscope (SEE), and more particularly, to an SEE with radial-line scanning on a two-dimensional (2D) sensor.

Description of the Related Art

Spectrally encoded endoscopy (SEE) is capable of making high resolution, real time imaging in ultra-miniature probes with diameter smaller than 1 mm. SEE uses a broad-bandwidth light source, miniature focusing optics and a diffraction grating to simultaneously focus multiple points along a traverse line within the sample and detect the reflectivity from the sample.

The SEE probe illuminates the sample with an array of focus spots, while each position, that is, each dispersion direction, is encoded with a different wavelength. Following transmission back through the optical fiber, the reflectance as a function of traverse location is determined by measured by scatter and reflected spectrum. The other dimension of the image is obtained by mechanically scanning the SEE probe at a slow rate, typically around 24 to 60 Hz. Light reflected from the sample can be detected with an imaging spectrometer with a high-speed line-scan sensor. When the line-scan sensor is used in a spectrometer, the spatial information in the scanning direction, that is, the direction perpendicular to the dispersion direction, is resolved by the fast read-out of the line sensor.

In general, the dispersed spectrum from a SEE probe is not uniformly scanning on the sample when the SEE probe rotates. That is, the sample is not equally sampled by the dispersed spectrum. However, as the detected spectrum from the sample is equally sampled on the sensor of the spectrometer, an under sampling issue could arise when the sampling theory fails at certain wavelength regions on the spectrometer.

SUMMARY

An apparatus for spectrally encoded endoscopy (SEE) is provided. The apparatus comprises an illumination element, a detection light guiding element, a rotary element, and a two-dimensional sensor. The illumination element is configured to direct an illumination light beam towards a sample. The detection light guiding element is configured to collect a reflected light beam from the sample. At least one of the illumination element and the detection light guiding element is configured to spectrally disperse the illumination light beam or the reflected light beam, respectively. The rotary element is configured to rotate or oscillate the reflected light beam. The two-dimensional sensor, wherein the reflected light beam is guided from the rotary element to the two-dimensional sensor.

In one embodiment, the detection light guiding element is stationary and the rotary element comprises a rotary junction. The rotary element may comprise a prism. Alternatively, the detection light guiding element may be rotated by the rotary element, and the illumination light beam may remain stationary. The rotary element may comprise a hollow shaft motor.

The apparatus may further comprise a spectrometer that comprises a collimating component, a dispersive component; and the two-dimensional sensor. The collimating element may comprise a collimating component and a focusing component.

The detection light guiding element may comprise a dispersive component disposed at the distal end of the detection light guiding element. The illumination element may comprise an illumination fiber, a focusing component; and a dispersive component disposed at the distal end of the illumination element to disperse the illumination light beam towards the sample. An illumination rotary junction may be included and configured to rotate the illumination light beam. The reflected light beam is rotated at a speed that is an integer multiple of the rotational speed of the illumination light beam. The reflected light beam and the illumination light beam are rotated at substantially the same speed. The illumination element comprises a multimode optical fiber, and the detection light guiding element comprises a single mode optical fiber.

In one embodiment, a pair of relay lenses configured to adjust image size at the two-dimensional sensor.

The rotary element may comprise a rotating grating configured to disperse the reflected light beam before incident on the two-dimensional sensor.

A method for obtaining radial scan in a spectrally encoded endoscope (SEE) is provided. An incident is projected incident light beam onto a sample. A reflected light beam from the sample is detected. The reflected light beam detected from the sample is dispersed. The dispersed incident light beam and the dispersed reflected light beam are rotated synchronously. The dispersed reflected light beam is guided onto a two-dimensional sensor.

An SEE probe including an illumination, a detection fiber, and a first dispersive element is provided. The illumination fiber is configured to guide the incident light beam from the light source onto the sample. The detection fiber is configured to guide the reflected light beam towards a spectrometer. The first dispersive element is configured to disperse light incident onto the sample or light reflected from the sample into a plurality of light rays. The method may further comprise rotating the illumination fiber and the detection fiber synchronously. The incident light beam may be dispersed before projecting onto the sample.

A SEE system is provided. The SEE system comprises an illumination element, a detection fiber, a rotary element, and a spectrometer. The illumination element may comprises an illumination fiber, a focusing component. and a dispersive component disposed at the distal end of the illumination element to disperse an illumination light beam directed towards a sample. The detection fiber is configured to collect a reflected light beam from the sample and forward the reflected light beam to the rotary element. The rotary element is configured to rotate or oscillate the reflected light beam. The spectrometer may comprise a collimating component, a dispersive component, configured to disperse the reflected light beam, and a two-dimensional sensor. The dispersed reflected light is guided from the rotary element to the spectrometer.

In the SEE system, the rotary device is configured to rotate the disperse illumination light beam and the reflected light beam synchronously. The detection fiber is stationary and wherein the rotary element comprises a rotary junction. The detection fiber is rotated by the rotary element. The SEE system may further comprise a rotary junction configured to rotate the illumination light beam.

BRIEF DESCRIPTION OF THE DRAWINGS

FIG. 1(c) Shows the detected signal of the dispersed light rays imaged on a line sensor in a spectrometers with the wavelengths equally sampled by sensor pixels;

FIG. 2(a) shows the dispersed light rays from the SEE radially scanning on the sample;

FIG. 2(b) shows the detected signal of the dispersed light rays scanning on a two-dimensional sensor in a spectrometer according to one embodiment of the current application;

DETAILED DESCRIPTION

The following description is of certain illustrative embodiments, although other embodiments may include alternatives, equivalents, and modifications. Additionally, the illustrative embodiments may include several novel features, and a particular feature may not be essential to practice the devices, systems, and methods described herein.

Figure 1A:
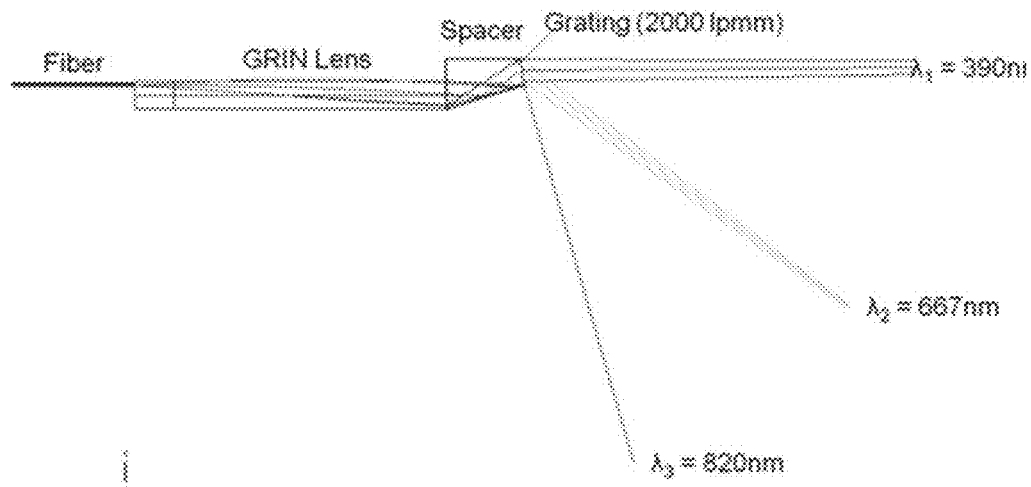
FIG. 1(a) shows an exemplary structure of a forward view SEE probe.
Figure 1B:
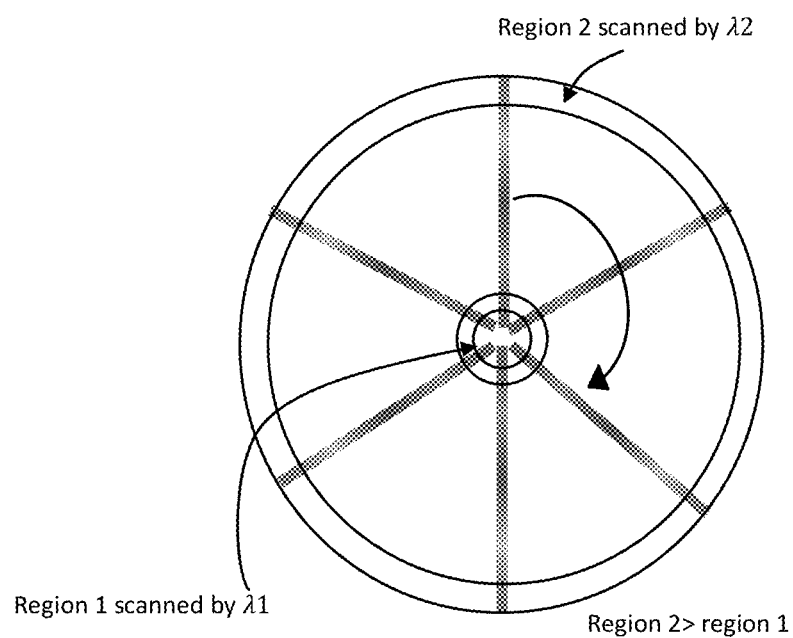
FIG. 1(b) shows the dispersed light rays from the SEE probe radially scanning on a sample.

For a forward-viewing SEE probe, one region of the dispersed spectrum, for example, the red ray scans on a much larger area of the sample than the other region such as the blue ray of the spectrum. If the wavelength is equally sampled on the sensor, the detected signal will be under-sampled in some regions of the spectrum and over-sampled on the others. FIG. s 1(a) to 1(c) illustrate such issue for a forward-view SEE probe. As shown in FIG. 1(a), as the SEE probe rotates, the dispersed rays are radially scanning on the sample. Region 2 sampled by wavelength $\lambda 2$, for example, at 667 nm, has an area much larger than the area of region 1 sampled by wavelength Xi, for example, at 390 nm, as shown in FIG. 1(b). However, the wavelengths are equally sampled by the same time interval of the line scan sensor in a spectrometer. As a result, the region 1 sampled by $\lambda 1$ is oversampled on the spectrometer, while the region 2 sampled by $\lambda 2$ is under sampled as shown in FIG. 1(c).

In a side view SEE probe system, a galvanometric scanner is typically used for slow axis (perpendicular to the dispersion direction) scanning of the spectrally encoded line by oscillating the SEE probe. In a forward view SEE probe, the probe, including illumination and/or detection fiber, is typically rotated 3600 continuously by a motor with an optical fiber rotary junction to avoid fiber entanglement. As shown in FIG. 1(a), a forward view SEE probe according to an embodiment of current application includes an illumination fiber extending to guide the light traveling through the SEE probe. The SEE probe may include a GRIN lens and a grating from which the light is dispersed into a plurality of light rays including, for example, a light ray with a wavelength $\lambda 1$ at about 390 nm, a light ray with a wavelength $\lambda 2$ at about 667 nm, and a light ray with a wavelength $\lambda 3$ at about 820 nm. As shown in FIG. 2(a), the dispersed light rays $\lambda 1$, $\lambda 2$, and $\lambda 3$ radially scan on a sample. To resolve the over- and under-sampling problems, the line scan of the detected signal of the dispersed light rays on the sensor as shown in FIG. 1(c) is preferably replaced with a radial scan such that the wavelength $\lambda 3$ falling on an outer region of a sensor is sampled more than the wavelength $\lambda 1$ falling on an inner region of the sensor as shown in FIG. 2(b).

Figure 3:
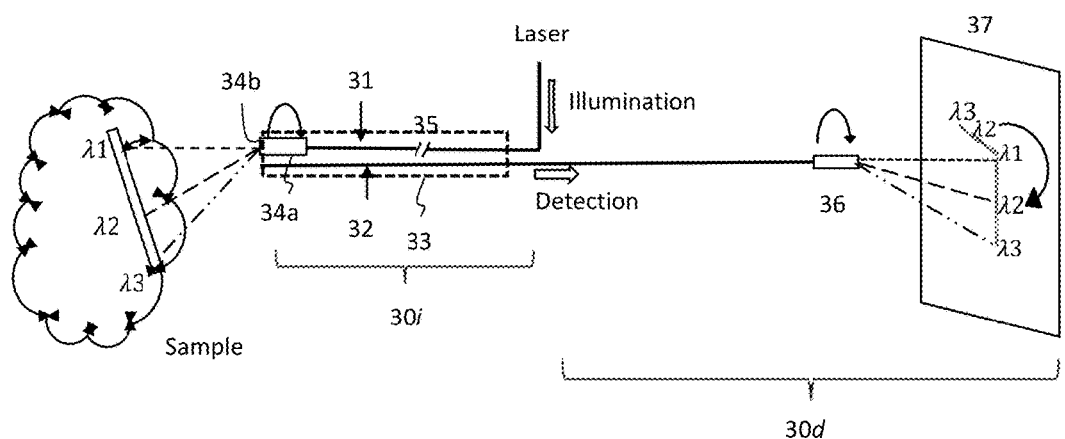
FIG. 3 shows a schematic drawing of a SEE system with a 2D sensor.

To achieve the radial scan of the detected signal on the sensor, a SEE system is provided as shown in FIG. 3. The SEE system includes a SEE probe 33 at a sample side 30i and an imaging spectrometer in the detection side 30d. The SEE probe 33 includes an illumination fiber 31, a detection fiber 32, an optics 34a such as a set of a spacer, a distal end optics including a GRIN lens, a ball, spherical and/or aspheric lens (see FIG. 1a), and a dispersive optics 34b such as a grating or a prism. The illumination fiber can be a single mode fiber while the detection fiber can be a multimode fiber. The illumination fiber 31 extends through the SEE probe 33 to guide light from a light source, for example, a laser or other illumination source, onto a sample. The light is dispersed by the dispersive optics 34b into light rays at various wavelengths. In the example as shown in FIG. 3, the dispersed light rays include $\lambda 1$, $\lambda 2$, and $\lambda 3$. The dispersed light rays reflected from the sample are detected by the detection fiber 32. The optics of imaging spectrometer may include the detection fiber 32 extending from the sample side 30i towards the image spectrometer at the detection side 30d, so as to guide the detected signals of the dispersed light rays $\lambda 1$, $\lambda 2$, and $\lambda 3$ from the sample to the spectrometer 36. In one embodiment, apart from the image sensor 37, the spectrometer may include a miniature structure, for example, a detection probe 36 with a structure similar to that of the optics 34a and 34b of the SEE probe 30. The detection probe 36 may include the detection fiber 32 extending from the sample side 30i, a dispersive optics such as grating or prism, collimating and focusing lenses such as GRIN, ball, spherical, and or aspheric lenses.

To achieve the radial scan of the detected signals on the two-dimensional sensor 37, the detection probe 36 rotates synchronously with the SEE probe 33. The detected dispersed light rays are imaged on the 2D sensor 37. The rotation speed of the detection probe 36 may be faster than a frame rate of the 2D sensor 37 to reduce the non-uniform rotational distortion (NURD). The high-speed rotation also prevents blackout area caused from read-out dead-time of the 2D sensor 37. The rotation of the detection probe 36 may be control/driven by the same motor driving the SEE probe 33. Alternatively, the rotations of the SEE probe 33 and the detection probe 36 can be driven and/or controlled by different motors.

In one embodiment, the illumination fiber 31 may be selected from a single-mode fiber, while the detection fiber can be selected from a multimode fiber. The number of detection fiber is not limited to one. The illumination fiber ₃1 is rotated by a motor with an optical fiber rotary junction 35. The detection fiber 32 is rotated together with the illumination fiber 31 to achieve the synchronous rotations of the SEE probe 33 and the detection probe 36 without the need of a rotary junction for the detection probe 36.

It will be appreciated that the illumination pattern of the detected dispersive light rays on the 2D sensor is not limited to the shapes as shown in FIG. 2(b). In situation that one wavelength, for example, λ1 is oversampled and over exposed during one exposure time on a very limited number of pixels, these pixels might be saturate and the dynamic range of the sensor might not be sufficient. A donut shape scanning pattern of the detected dispersive light rays may be provided to mitigate this issue.

Figure 4:
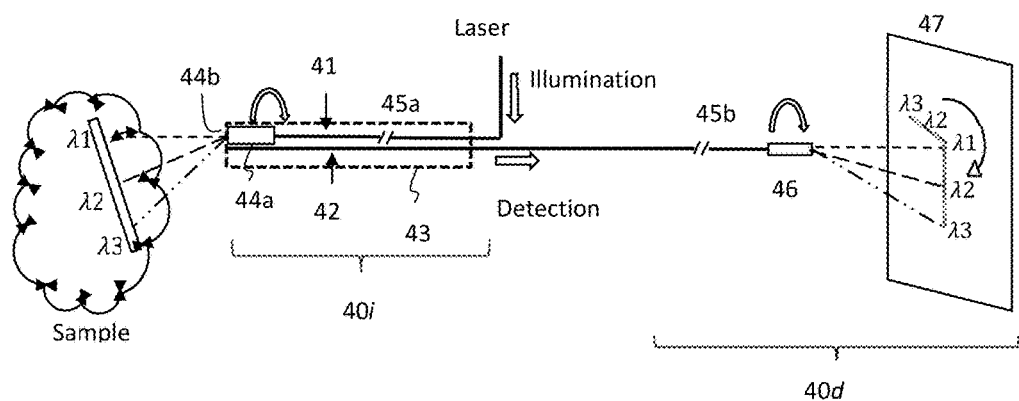
FIG. 4 shows a schematic drawing of a SEE system with a 2D sensor according to another embodiment.

FIG. 4 shows a SEE system according to another embodiment. Similar to the SEE system as shown in FIG. 3, the SEE system includes an SEE probe 43 at a sample side 40i and an imaging spectrometer 46 in the detection side 40d. The illumination side 40i includes an illumination fiber 41, a detection fiber 42, and an SEE probe 43 through which the illumination fiber 41 and the detection fiber 42 extend. The SEE probe 43 may include an optics 44a such as a set of a spacer, a distal end optics including a GRIN lens, a ball, spherical and/or aspheric lens (see FIG. 1a), and a dispersive optics 44b such as a grating or a prism. The illumination fiber 41 extends through the SEE probe 43 to guide light from a light source, for example, a laser or other illumination source, towards a distal end of the SEE probe 43. The light is dispersed into multiple light rays at various wavelengths by the dispersive optics 44b incident onto the sample. In the example as shown in FIG. 4, the dispersed light rays include λ1, λ2, and λ3. The dispersed light rays reflected from the sample are detected by the detection fiber 42. The optics of imaging spectrometer may include the detection fiber 42 extending from the illumination side 40i towards an image spectrometer, so as to guide the detected signals of the dispersed light rays λ1, λ2, and λ3 from the sample to the image spectrometer 46. In one embodiment, apart from the image sensor 47, the spectrometer may include a miniature structure, for example, a detection probe $_4$6 with a structure similar to that of the optics 44a and 44b of the SEE probe 43. The reflected light guided by the detection fiber 42 travels from the illumination side $_{40}$1 through a dispersive optics such as grating or prism, collimating and focusing lenses such as GRIN, ball, spherical, and or aspheric lenses of the detection probe 46 before being incident on the image sensor 47.

In the embodiment as shown in FIG. 4, the illumination fiber 41 and the detection fiber 42 on the detection side 40d are controlled and driven by different motors. This way, the illumination fiber 41 may rotate while the detection fiber 42 on the sample side 40i remains stationary. To prevent the entanglement between the illumination fiber 41 and the illumination fiber from the laser or other light source, a rotary junction 45a is installed in the SEE probe 43. A rotary junction 45b is also installed in the detection probe 46 to allow the detection fiber 42 on the detection side 40d to rotate independently from the illumination fiber 41. The structure as shown in FIG. 4 is advantageous when the detection fiber 42 is long and flexible. Although the rotations of the illumination fiber 41 and the detection fiber 42 on the detection side 40d can be independently controlled, synchronous rotations between the illumination fiber 41 and the detection fiber 42 is still desired.

Figure 5:
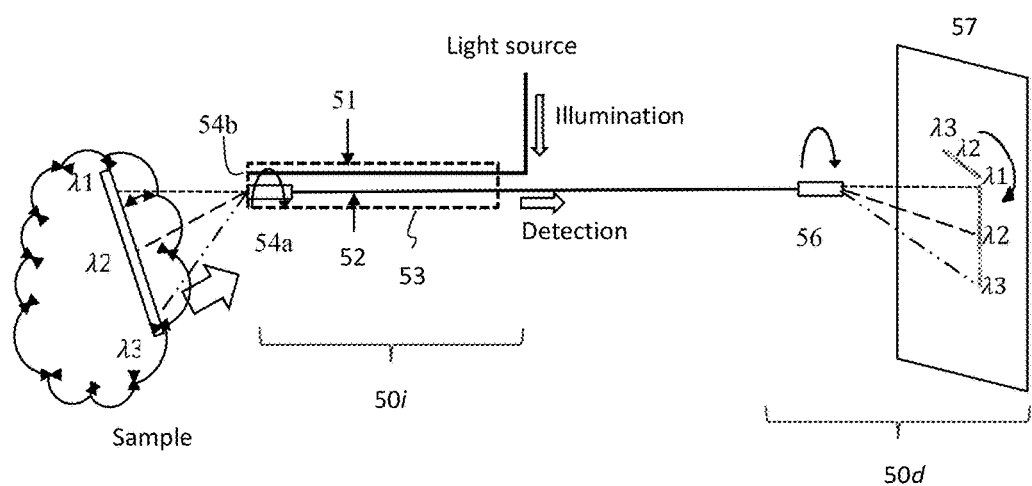
FIG. 5 shows a schematic drawing of a SEE system with a 2D sensor according to another embodiment.

FIG. 5 shows a SEE system according to another embodiment. Similar to the SEE system as shown in FIG. 3, the SEE system includes an SEE probe 53 at a sample side 50Ii and an imaging spectrometer 56 in the detection side 50d. The SEE probe 53 at the illumination side 50i includes an illumination fiber 51 and a detection fiber 52. The SEE probe 53 may include a set of optics 54a consisting of a spacer, a distal end optics including a GRIN lens, a ball, spherical and/or aspheric lens, and a dispersive device such as a grating or a prism 54b. In the current embodiment, the set of optics 54 is mounted at the tip of the detection fiber 52 instead of the illumination fiber 51. The illumination fiber 51 guides light from a light source, for example, a laser or other illumination source, towards the sample. The light reflected from the sample is dispersed and collected by the optics 54 mounted at the tip of the optic fiber and guided by the detection fiber 52 towards the image spectrometer 56. The optics of imaging spectrometer 56 may include the detection fiber 52 extending from the illumination side 50i towards an image spectrometer, so as to guide the detected signals of the dispersed light rays λ1, λ2, and λ3 from the sample to the image spectrometer 56. In one embodiment, apart from the image sensor 57, the spectrometer may include a miniature structure, for example, a detection probe 56 with a structure similar to that of the optics 54a and 54b of the SEE probe 53. The reflected light guided by detection fiber 52 travels from the illumination side 50i through a dispersive optics such as grating or prism, collimating and focusing lenses such as GRIN, ball, spherical, and or aspheric lenses of the detection probe 56 before being incident on the image sensor 57.

In the embodiment as shown in FIG. 5, the illumination fiber 51 includes a multimode fiber, while the detection fiber 52 may include a single-mode fiber. The optics 54a including spacer, the lenses (GRIN/ball/spherical/aspheric lenses), dispersive optics 54b such as grating and/or prism, are attached to the distal end of the detection fiber 52. The illumination fiber 51 can stay stationary while the detection fiber 52 rotates, and the detection fiber 52 and the detection probe 56 rotate at the same speed. In another embodiment, the reflected light beam may be rotated at a speed as an integer multiple of the rotation speed of the illumination light beam. In FIG. 5, the rotation speed of the detection fiber 52 and the detection probe 56 are so controlled such that the rotation speeds of the detection fibers 52 and probe 56 are substantially the same, for example, with a difference no more than 5% between each other. As a result, no rotary junction is required by the structure as shown in FIG. 5.

Figure 6:
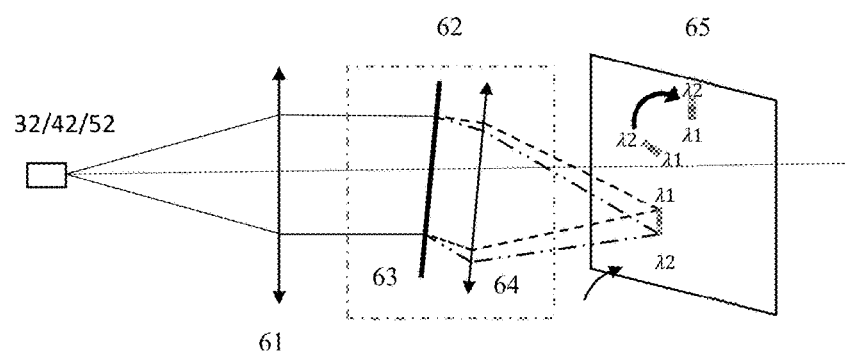
FIG. 6 shows an exemplary structure of the spectrometer used for achieving radial scan on the 2D sensor.

FIG. 6 shows an embodiment of the spectrometer at the detection side of an SEE system. As shown, the spectrometer includes a collimating lens 61 for collimating the light rays from the detection fiber, for example, the detection fiber 32, 42, or 52 as shown in FIG. 3, 4, or 5. The rotating part 62 of the spectrometer includes a dispersive device 63, for example, a grating, and a focusing lens 64 for rotating the collimated light rays before incident onto the 2D sensor 65, so as to achieve a radial scan of the images.

Figure 7:
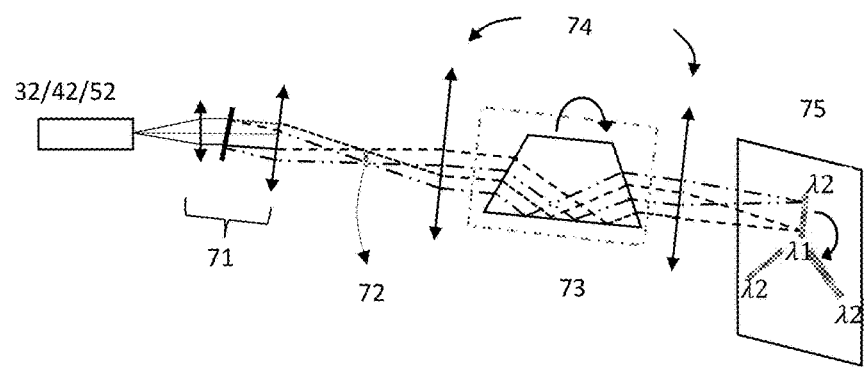
FIG. 7 shows another exemplary structure of the spectrometer used for achieving radial scan on the 2D sensor

FIG. 7 shows another embodiment of the spectrometer in the detection side of the SEE system. As shown, the spectrometer includes a set of optics 71 for forming an intermediate image 72, a rotatable prism 73 rotating to create a radial scan on the 2D image sensor 75, and the 2D image sensor 75. The spectrometer may also include a pair of relay lenses 74 to adjust the size of the image to fit the size of the 2D sensor 75.

Figure 8:
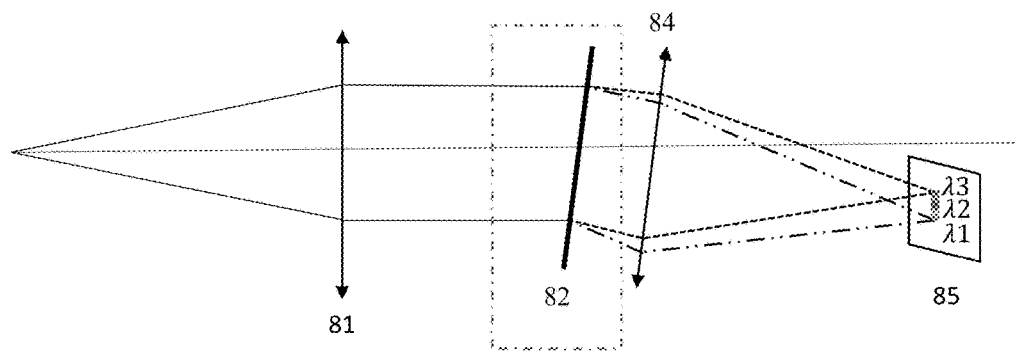
FIG. 8 shows another exemplary structure of the spectrometer used for achieving radial scan on the 2D sensor.

FIG. 8 shows another embodiment of the spectrometer in the detection side of the SEE system. Similar to the spectrometer as shown in FIG. 6, the spectrometer includes a collimating lens 81 to collimate light rays from a detection fiber, for example, the detection fiber 32, 42, and 52 as shown in FIGS. 3-5, a dispersive device 82 such as a grating, and a focusing lens 84. In the current embodiment, the dispersive device 82 itself is rotating to achieve the radial scan on the image sensor 85.

Figure 9:
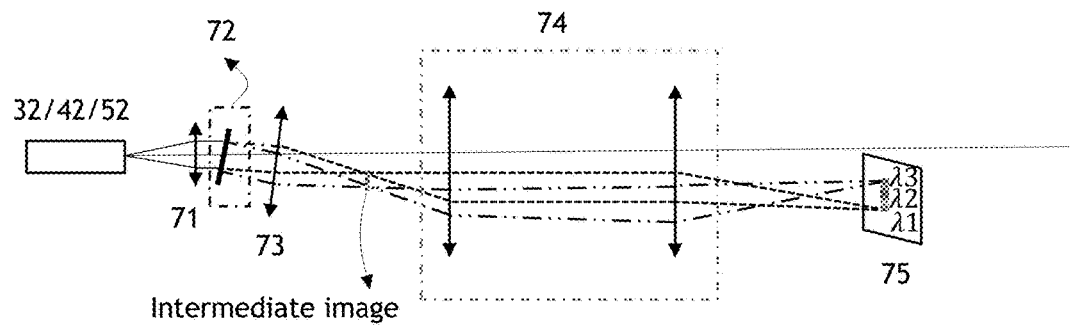
FIG. 9 shows another exemplary structure of the spectrometer used for achieving radial scan on the 2D sensor.

FIG. 9 shows another embodiment of the spectrometer. As shown, the spectrometer includes a collimator 91, a grating 92, and a focusing lens 93 for forming an intermediate image. The spectrometer further comprises a pair of relay lenses 94 for adjust magnification of the image projected on the 2D sensor 95. In this embodiment, the grating 92 in front of the detection fiber rotates, preferably synchronously with the dispersive light rays entering the detection fiber. It will be appreciated that the spectrometers as shown in FIGS. 6-8 can be used in combination with any of the SEE probes 33, 43, and 53 as shown in FIGS. 3-5, respectively.

Figure 10:
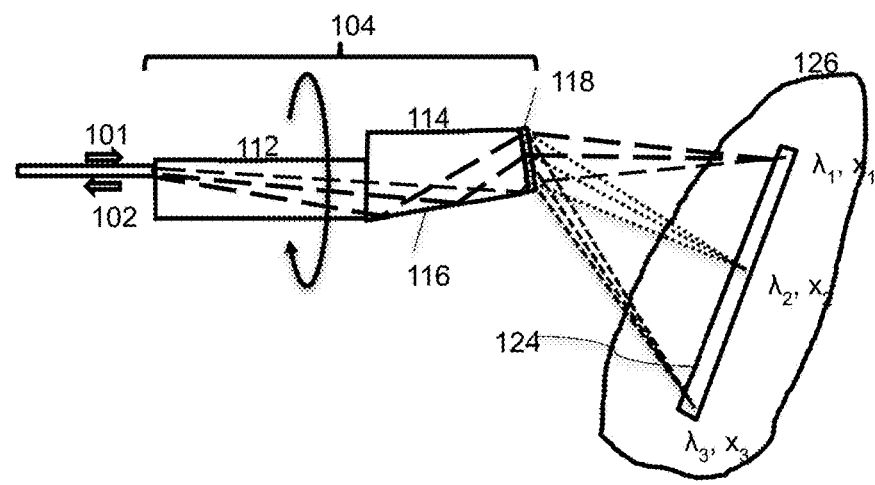
FIG. 10 shows a schematic of an exemplary SEE color probe.

An exemplary embodiment of a SEE probe that can be used in accordance with the present disclosure is shown in FIG. 10. The SEE probe includes an illumination fiber 101 and optics 104 including a focusing component 112 depicted here as a gradient index (GRIN) lens, a spacer 114 having a surface acting as a mirror or other reflector 116, and a dispersive component 118, which may be a grating. Broadband light (or other electro-magnetic radiation) can be coupled or otherwise provided into the illumination fiber 101. The illumination fiber 101 is configured to guide the light to the optics 104 of the SEE probe such as through the fiber core mode. The illumination fiber 101 which can be or include, for example, a single-mode fiber, a-few-mode fiber, or a multi-mode fiber. The outer diameter of a fiber cladding of the fiber can be, for example 100 µm, 125 µm, or 200 µm, and may be modified if desired. The light is a mixture of various wavelengths that is generally in the visible spectrum, and may also extend into the UV or near IR, as well as into other ranges. The exemplary range of the wavelength can be typically from 400 nm to 800 nm or to 1000 nm. The light (or other electro-magnetic radiation) can be slightly focused after passing though the light focusing component. When the light passes through the probe, it can, for example, propagate in a transparent media against the input wavelength. In some embodiments, the fiber is double clad fiber, the typical core diameter is less than 10 µm. The fiber may be used for both illumination 101 and detection 102.

The focusing component 112 may be, for example, a GRIN lens which almost collimates but slightly focuses the light. Alternatively, other focusing component(s), such as micro lens(es), can be used instead of a GRIN lens. The spacer 114 of this embodiment can be, for example, air, glass, or epoxy and is normal-polished at the proximal end, and angle-polished at the distal end shown in FIG. 10. The spacer 114 also includes an angle-polished surface 116 that can be used as mirror when light from the lens 112 is incident on the surface 116. This angle-polished surface 116 can have, for example, a metallic or dielectric coating to increase the reflectivity thereof. The lens 112 can be GRIN lens. The lens 112 is attached to the spacer 114 proximal end. The spacer's distal end, which has been angle-polished, is used as a base for a dispersive element 118 that is shown as a grating. The dimensions of the spacer 114 are determined so that the light coming through the focusing component 112 is reflected by one of the angled surface 116, and goes into the dispersing component 118. The dispersing component 118 is depicted as a grating that is located directly on the spacer 114. The grating can have various forms, such as, e.g., standard groove grating, blazed grating, or volume grating including holographic grating and so on. The dispersive component 118 may be a prism. The dispersive component 118 diffracts light into spectrally encoded line 124 which is shown incident on a tissue sample 126.

Light returned from the target may be detected by the same optics and is thus delivered to a spectrometer through the optical fiber 102. Thus, light (or other electro-magnetic radiation) reflected by the tissue 126 can be coupled or otherwise provided back to the fiber 102, and then can be delivered to a spectrometer. Other SEE optical components may be used as well. For example, the apparatus and methods as described herein may be used with the exemplary SEE systems described, for example, in U.S. Pat. Nos. 6,341,036; 7,447,408; 7,551,293; 7,796,270; 7,859,679; 8,045,177; 8,145,018; 8,838,213; 9,254,089; 9,295,391; 9,415,550; 9,557,154 and Patent Application Publication Nos. US2017/0035281; WO2015/116951; WO2015/116939; WO2017/024145; and U.S. Non-Provisional patent application Ser. No. 15/418,329 filed Jan. 27, 2017 each of which patents and patent publications are incorporated by reference herein in their entireties.

Figure 11:
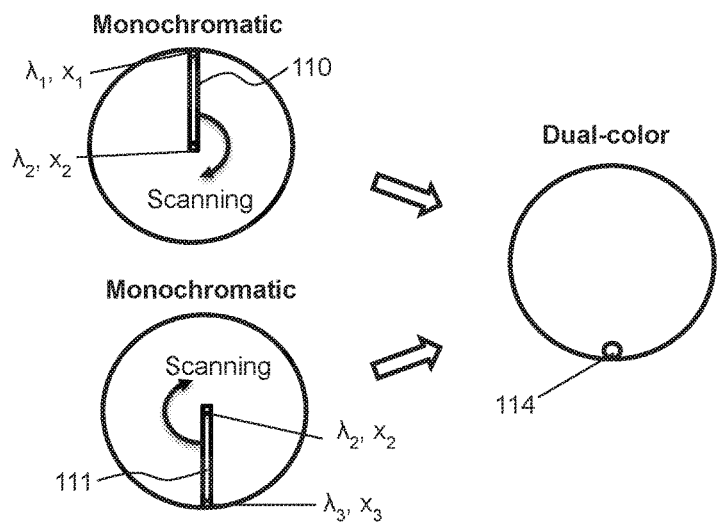
FIG. 11 shows the detected signal of the dispersed light rays for two monochromatic images that are combined to form a color image.

FIG. 11 shows designs utilizing the rotation motion of the dispersion on the sample to generate images. In this illustration, a dual-color image is obtained by the SEE probe according to various exemplary embodiments of the present disclosure. In this example, a monochromatic image can be obtained by scanning the first spectrally-encoded line 110. Another monochromatic image can be obtained by scanning the second spectrally-encoded line 111. The exemplary (e.g., two) monochromatic images can be combined to generate a dual-color image as shown on the right side of FIG. 11, where each point has been imaged by two wavelengths of light, as exemplified by point 114, which was imaged by light at wavelengths $\lambda_1$ and $\lambda_3$.

In some embodiments, the sensor of the spectrometer may include a 2D RGB, for example, a Bayer array sensor. In other embodiments, the detection side may have three monochromatic 2D sensor and three sets of rotation mechanisms. The spectrometer can be designed similar to the detection probe as shown in FIGS. 3-5, such that the center or the part close to the center of a dispersion line is the rotational scanning axis. The 2D sensor includes a color sensor.

There are many ways to achieve images based on the radial scanning as described herein. In at least one embodiment, a computer, may be dedicated to control and monitor the SEE apparatus, systems, and methods described herein.

Various components of a computer system 1200 (see e.g., the console or computer 1200 as described above are provided in FIG. 12. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines between one or more of the aforementioned components. In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a SEE device or systems for performing radial scanning SEE. The CPU 1201 is configured to read and perform computer-executable instructions stored in a storage medium. The computer-executable instructions may include those for the performance of the methods and/or image processing described herein. The computer system 1200 may include one or more additional processors in addition to CPU 1201, and such processors, including the CPU 1201, may be used for creating images from the radial scanning SEE system as described herein. The system 1200 may further include one or more processors connected via a network connection (e.g., via network 1206). The CPU 1201 and any additional processor being used by the system 1200 may be located in the same telecom network or in different telecom networks (e.g., performing SEE technique(s) may be controlled remotely).

Figure 12:
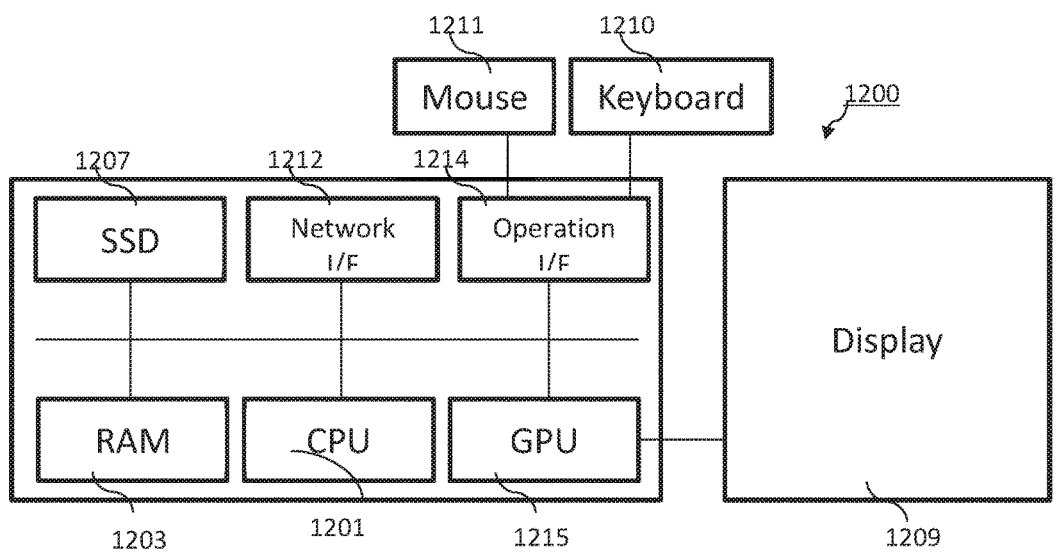
FIG. 12 shows a computer system used with the SEE system according to another embodiment.

The I/O or communication interface 1205 provides communication interfaces to input and output devices, which may include the light source 1201, a spectrometer, a microphone, a communication cable and a network (either wired or wireless), a keyboard 1210, a mouse (see e.g., the mouse 1211 as shown in FIG. 12), a touch screen or screen 1209, a light pen and so on. A monitor or display interface or screen 1209 provides communication interfaces thereto.

Any methods and/or data of the present disclosure, such as the methods for performing the radial line scanning as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 12), SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the apparatus, system, and method related to the processors, such as, but not limited to, the processor of the aforementioned computer 1200, the processor of computer 1200', etc., as described above may be achieved utilizing suitable hardware, such as that illustrated in the figures. Functionality of one or more aspects of the present disclosure may be achieved utilizing suitable hardware, such as that illustrated in FIG. 12. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 12) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

As aforementioned, hardware structure of an alternative embodiment of a computer or console 1200' is shown in FIG. 12. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid state drive (SSD) 1207. Preferably, the computer or console 1200' includes a display 1209. The computer 1200' may connect with the rotary element (e.g., 34, 36, 44, 46, etc.), the at least one detector (e.g., 30*d*, 40*d*, 50*d*, etc), the MCU and/or the spectrometer via the operation interface 1214 or the network interface 1212. A computer, such as the computer 1200', may include the MCU in one or more embodiments. The operation interface 1214 is connected with an operation unit such as a mouse device 1211, a keyboard 1210 or a touch panel device. The computer 1200' may include two or more of each component. Alternatively, the CPU 1201 or the GPU 1215 may be replaced by the field-programmable gate array (FPGA), the application-specific integrated circuit (ASIC) or other processing unit depending on the design of a computer, such as the computer 1200, the computer 1200', etc.

A computer program is stored in the SSD 1207, and the CPU 1201 loads the program onto the RAM 1203, and executes the instructions in the program to perform one or more processes described herein, as well as the basic input, output, calculation, memory writing and memory reading processes.

The computer, such as the computer 1200, 1200', communicates with the rotary element (e.g., 34, 36, 44, 46, etc.) and/or the MCU to perform imaging, and reconstructs an image from the acquired intensity data. The monitor or display 1209 displays the reconstructed image, and may display other information about the imaging condition or about an object to be imaged. The monitor 1209 also provides a graphical user interface for a user to operate a SEE system (e.g., the system 100, the system 100', the system 100", the system 1100, etc.). An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs the system to set or change the imaging condition, and to start or end the imaging. The illumination element, rotary element, spectrometer, two dimensional sensor, and/or one or more other components of any of the systems discussed herein may have interfaces to communicate with the computers 1200, 1200' to send and receive the status information and the control signals.

While the above disclosure describes certain illustrative embodiments, the invention is not limited to the above-described embodiments, and the following claims include various modifications and equivalent arrangements within their scope.

What is claimed is:

1. An apparatus for spectrally encoded endoscopy (SEE) comprising:
   an illumination light guiding element configured to direct an illumination light beam towards a sample;
   a detection light guiding element configured to collect a reflected light beam from the sample, wherein at least one of the illumination light guiding element and the detection light guiding element is configured to spectrally disperse the illumination light beam or the reflected light beam, respectively, into a spectrally encoded line;
   a rotary element configured to rotate or oscillate the reflected light beam; and
   a two-dimensional sensor, wherein the dispersed reflected light beam is guided from the rotary element to the two-dimensional sensor, such that the spectrally encoded line scans the two-dimensional sensor.

2. The apparatus according to claim 1, wherein the rotary element comprises a rotary junction, and wherein the detection light guiding element includes an optical fiber.

3. The apparatus according to claim 2, wherein the rotary element further comprises one or more of a prism, a grating, and a lens, and wherein the rotary junction transfers the reflected light beam from the stationary fiber to the one or more of a prism, a grating, and a lens.

4. The apparatus according to claim 1, wherein the detection light guiding element is rotated by the rotary element.

5. The apparatus according to claim 4, wherein the rotary element comprises a hollow shaft motor.

6. The apparatus according to claim 4, wherein the illumination light beam remains stationary.

7. The apparatus according to claim 1, further comprising a spectrometer, the spectrometer comprising:
   a collimating component;
   a dispersive component; and
   the two-dimensional sensor.

8. The apparatus according to claim 7, wherein the collimating component comprising a collimating element and a focusing element.

9. The apparatus according to claim 1, wherein the detection light guiding element comprises a dispersive component disposed at the distal end of the detection light guiding element.

10. The apparatus according to claim 1, wherein the illumination light guiding element comprises:
    an illumination fiber;
    a focusing component; and
    a dispersive component disposed at the distal end of the illumination fiber to disperse the illumination light beam directed towards the sample.

11. The apparatus according to claim 1, further comprising an illumination rotary junction configured to rotate the illumination light beam.

12. The apparatus according to claim 11, wherein the reflected light beam is rotated at a speed that is substantially the same as an integer multiple of the rotational speed of the illumination light beam.

13. The apparatus according to claim 11, wherein the reflected light beam and the illumination light beam are rotated independently from each other.

14. The apparatus according to claim 1, wherein the illumination light guiding element comprises a multimode optical fiber or a single mode optical fiber, and the detection light guiding element comprises one or more a single mode optical fiber and/or one or more of a multimode optical fiber.

15. The apparatus according to claim 1, further comprising a pair of relay lenses configured to adjust an image size of the spectrally encoded line projected on the two-dimensional sensor.

16. The apparatus according to claim 1, wherein the rotary element comprises a rotating grating configured to disperse the reflected light beam into the spectrally encoded line before the reflected light beam is incident on the two-dimensional sensor.

17. The apparatus according to claim 1, wherein the rotary element rotates or oscillates the reflected light beam so that the spectrally encoded line scans the two-dimensional sensor in a rotating or oscillating manner.

18. The apparatus according to claim 1, wherein the rotary element oscillates the reflected light beam so that the spectrally encoded line scans the two-dimensional sensor in a linear direction perpendicular to the dispersion direction of the spectrally encoded line.

19. The apparatus according to claim 1, wherein the rotary element rotates the reflected light beam so that the spectrally encoded line scans the two-dimensional sensor in a circular direction with a radial scan such that a first wavelength of the reflected light beam falling on an outer region of the two-dimensional sensor is sampled more than a second wavelength falling on an inner region of the two-dimensional sensor.

20. A method for obtaining radial scan in a spectrally encoded endoscope (SEE), comprising:
    projecting an incident light beam onto a sample;
    detecting a reflected light beam from the sample;
    dispersing the reflected light beam detected from the sample; and
    rotating the dispersed incident light beam and the dispersed reflected light beam synchronously; and
    guiding the dispersed reflected light beam onto a two-dimensional sensor.

21. The method according to claim 20, further comprising providing an SEE probe including:
    an illumination fiber configured to guide the incident light beam from the light source onto the sample;
    a detection fiber configured to guide the reflected light beam towards a spectrometer; and
    a first dispersive element configured to disperse light incident onto the sample or light reflected from the sample into a plurality of light rays.

22. The method according to claim 21, further comprising rotating the illumination fiber and the detection fiber synchronously.

23. The method according to claim 21, further comprising dispersing the incident light beam before projecting onto the sample.

24. A spectrally encoded endoscope (SEE) system, comprising:
an illumination light guiding element comprising:
   an illumination fiber;
   a focusing component; and
   a dispersive component disposed at the distal end of the illumination light guiding element to disperse an illumination light beam directed towards a sample;
a detection fiber configured to collect a reflected light beam from the sample and forward the reflected light beam to a rotary element;
the rotary element configured to rotate or oscillate the reflected light beam; and
a spectrometer comprising:
   a collimating component;
   a dispersive component, configured to disperse the reflected light beam into a spectrally encoded line; and
   a two-dimensional sensor,
   wherein the dispersed reflected light beam is guided from the rotary element to the spectrometer, such that the spectrally encoded line scans the two-dimensional sensor.

25. The SEE system according to claim 24, wherein the rotary element is configured to rotate the dispersed illumination light beam and the reflected light beam synchronously.

26. The SEE system according to claim 24, wherein the detection fiber is stationary and wherein the rotary element comprises a rotary junction.

27. The SEE system according to claim 24, wherein the detection fiber is rotated by the rotary element.

28. The SEE system according to claim 24, further comprising a rotary junction configured to rotate the illumination light beam.

* * * * *